United States Patent [19]
Belagaje et al.

[11] Patent Number: 5,576,190
[45] Date of Patent: Nov. 19, 1996

[54] BACTERIOPHAGE LAMBDA PL PROMOTERS

[75] Inventors: Rama M. Belagaje, Indianapolis; Charles L. Hershberger, New Palestine; Hansen M. Hsiung, Carmel; Paul R. Rosteck, Jr.; Jane L. Sterner, both of Indianapolis, all of Ind.

[73] Assignee: Eli Lilly and Company, Indianapolis, Ind.

[21] Appl. No.: 156,325

[22] Filed: Nov. 23, 1993

Related U.S. Application Data

[63] Continuation of Ser. No. 511, Jan. 4, 1993, abandoned, which is a continuation of Ser. No. 739,280, Aug. 1, 1991, abandoned, which is a continuation-in-part of Ser. No. 565,783, Aug. 13, 1990, abandoned.

[51] Int. Cl.$^6$ .......................... C12N 1/21; C12N 15/11; C12N 15/67; C12N 15/73
[52] U.S. Cl. .................... 435/69.1; 435/252.33; 435/320.1; 536/24.1; 935/31; 935/39; 935/41; 935/43
[58] Field of Search .................. 435/69.1, 69.7, 435/69.8, 172.3, 320.1, 235.1, 252.3, 252.33; 536/23.1, 23.51, 24.1; 935/29, 31, 39, 41, 43

[56] References Cited

U.S. PATENT DOCUMENTS 4,874,703  10/1989  Jaskunas ........................ 435/252.33

FOREIGN PATENT DOCUMENTS 0058002  8/1982  European Pat. Off. .
0314274  5/1989  European Pat. Off. .

OTHER PUBLICATIONS

Jones, et al., 1982, *Mol. Gen. Genet.*, 188:486.

Sarai, 1989, *Proc. Natl. Acad. Sci. USA*, 86:6513.

Ensley, B. D., 1986, *CRC Crit. Rev. Biotechnol.*, 4(3):263.

Kusano, et al., 1989, *J. Mol. Biol.*, 209:623.

Szardenings, M., et al., 1990, *Gene*, 94:1–7.

Szardenings, M., et al., Apr. 9, 1990, *Genbank*.

Brandt, M. E., et al., Jul. 11, 1990, *Genbank*.

*Primary Examiner*—Dian C. Jacobson
*Attorney, Agent, or Firm*—Thomas G. Plant

[57] ABSTRACT

The present invention concerns novel DNA compounds which function as transcriptional activating sequences. Recombinant DNA expression vectors which contain the transcriptional activating sequences and host cells transformed with these expression vectors are also provided. When properly positioned in an expression vector, the novel transcriptional activating sequences enable regulatable expression of an operably linked gene and enhance the structural stability of the expression vector.

26 Claims, 7 Drawing Sheets

Restriction and Function Map of
pCZR125

Restriction and Function Map of
pHPR97

Restriction and Function Map of pHPR104

Restriction and Function Map of pHDM159

Restriction and Function Map of pHPR106

Restriction and Function Map of psynC

Restriction and Function Map of psynD 5,576,190

BACTERIOPHAGE LAMBDA PL PROMOTERS

CROSS REFERENCE TO RELATED APPLICATIONS

This application is a continuation of application Ser. No. 08/000,511, filed on Jan. 4, 1993, now abandoned, which is a continuation of application Ser. No. 07/739,280, filed on Aug. 1, 1991, now abandoned, which is a continuation-in-part of application Ser. No. 07/565,783, filed Aug. 13, 1990, now abandoned.

BACKGROUND AND SUMMARY OF THE INVENTION

Structural instability of recombinant DNA expression vectors results in DNA deletions and rearrangements that alter vector structure. This is a significant concern in large scale cultures grown to produce polypeptides encoded by these expression vectors. These vectors may be altered in a way that prevents expression of the encoded polypeptide. Thus, when the cultures are induced for expression of the polypeptide, a negative selective pressure toward a lack of polypeptide expression often results in an accumulation of the altered expression vectors.

In view of the above, regulatory agencies, such as the Food and Drug Administration, require full characterization of any recombinant DNA expression vectors that are utilized to produce heterologous proteins. Evidence must be submitted to verify that the recombinant DNA expression vector is the same at the end of the fermentation as the expression vector from the original inoculum. Certification data includes structural and size analysis of the expression, and verification of the nucleotide sequence that codes for the desired product, and the regions flanking this coding sequence, especially flanking sequences that perform important functions, such as promoters.

Recombinant DNA vectors which utilize the *Escherichia coli* bacteriophage lambda pL promoter-operator region to enable transcription of an operably linked gene are often plagued by structural instability. When such vectors are examined at the end of the fermentation process, the structure of the vectors is often altered. It is the purpose of the present invention to provide transcriptional activating sequences that enhance the stability of the expression vectors while providing regulatable transcription of an operably linked gene.

For the purpose of the present invention, as disclosed and claimed herein, the following terms are as defined below:

ApR—the ampicillin resistant phenotype or gene conferring the same.

cI857—the gene encoding a temperature sensitive form of the bacteriophage lambda cI repressor.

EK-Bovine Growth Hormone—methionyl-phenylalanyl-(aspartyl)$_4$-lysinyl-bovine growth hormone, with indicated amino-terminal amino acid sequence phenylalanyl-(aspartyl)-$_4$-lysinyl specifying an enterokinase cleavage site.

EK-BGH—EK-Bovine Growth Hormone

Functional Polypeptide—A recoverable, biologically active heterologous or homologous polypeptide or precursor, a recoverable bioactive polypeptide comprised of a heterologous polypeptide and a partial or whole homologous polypeptide, or a recoverable bioinactive polypeptide containing a heterologous polypeptide and a bio-inactivating polypeptide which can be specifically cleaved or a bioinactive polypeptide that can be converted to a bioactive polypeptide by refolding or other chemical treatments known to those skilled in the art.

pL—bacteriophage lambda leftward promoter.

Promoter—a DNA sequence that directs transcription of DNA into RNA.

Recombinant DNA Expression Vector—any recombinant DNA cloning vector into which a promoter has been incorporated.

Recombinant DNA Cloning Vector—any agent including, but not limited to, recombinant plasmids, bacteriophages, and viruses, consisting of a DNA molecule to which one or more additional DNA segments can or have been added.

Structural Gene—any DNA sequence that encodes a functional polypeptide, inclusive of that DNA encoding the start and stop codons.

TetR—the tetracycline resistant phenotype or gene conferring the same.

Transcriptional Activating Sequence—a DNA sequence that directs the transcription of DNA in a regulatable fashion.

Translational Activating Sequence—any DNA sequence, including the ribosome binding site and translational start codon, such as 5'-ATG-3', but not including any sequences downstream from the start codon, that provides for the initiation of translation of a mRNA transcript into a peptide or polypeptide.

DETAILED DESCRIPTION OF THE INVENTION

Figure 1:
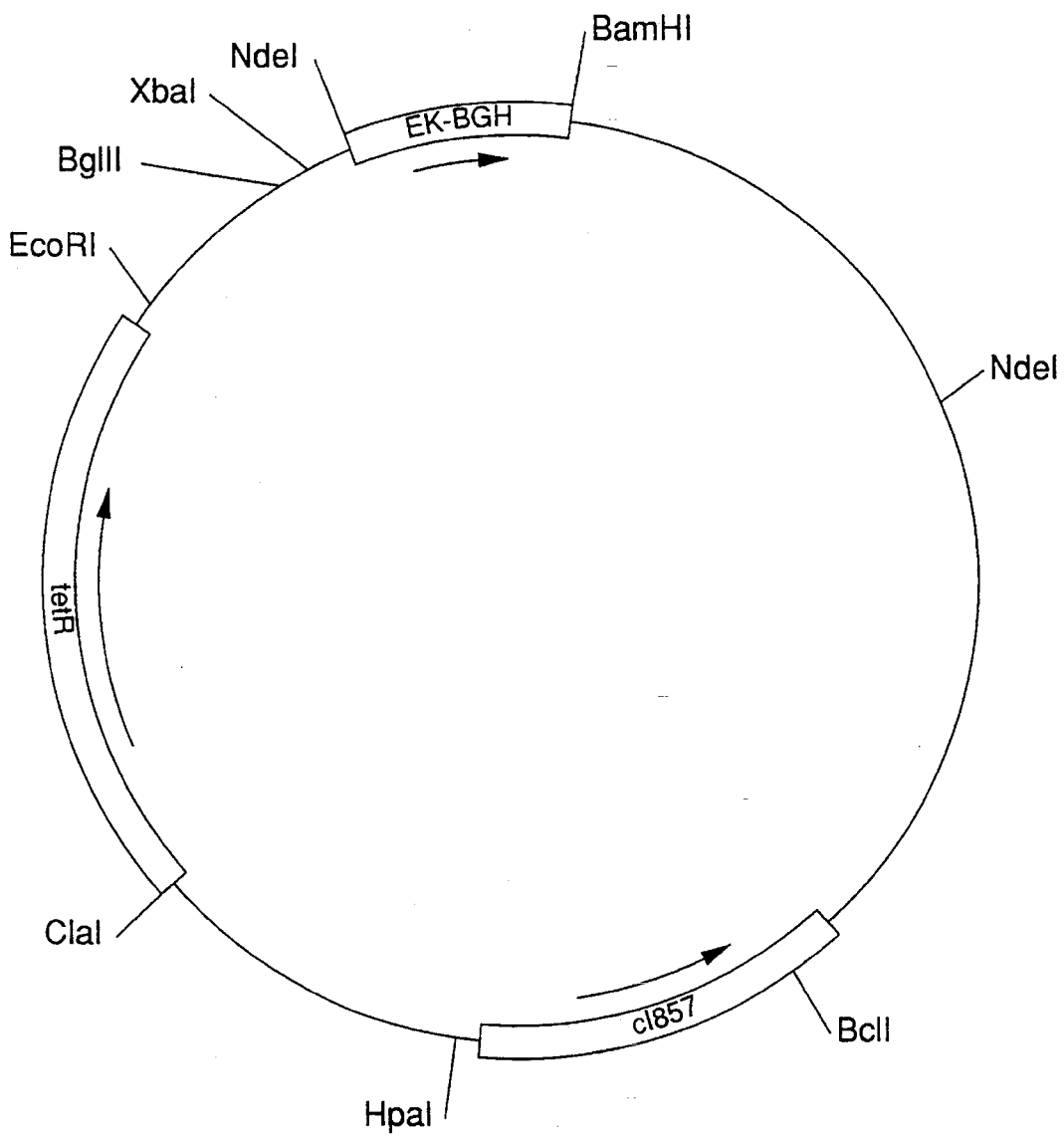
FIG. 1 is a restriction site and function map of plasmid pCZR125.

The present invention concerns novel transcriptional activating sequences, recombinant DNA expression vectors which comprise the novel transcriptional activating sequences, and host cells transformed with the expression vectors of the present invention. The transcriptional activating sequences of the present invention are modified bacteriophage lambda transcriptional activating sequences wherein the DNA sequence located in a position 5' to the repressor binding region has been deleted. The modified transcriptional activating sequence provides regulatable expression of an operably linked gene and confers structural stability upon the recombinant DNA vector into which it is cloned.

The preferred transcriptional activating sequences of the present invention have the following structures:

```
5'-CATACAGATAACCATCTGCGGTGATAAATTATCTCTGGCGGTGTTGACA
   ||||||||||||||||||||||||||||||||||||||||||||||||
3'-GTATGTCTATTGGTAGACGCCACTATTTAATAGAGACCGCCACAACTGT

TAAATACCACTGGCGGTGATACTGAGCACATCA-3'
|||||||||||||||||||||||||||||||||
ATTTATGGTGACCGCCACTATGACTCGTGTAGT-5';

5'-CATACAGATAACCATCTGCGGTGATAAATTATCTCTGGCGGTGTTGACA
   ||||||||||||||||||||||||||||||||||||||||||||||||
3'-GTATGTCTATTGGTAGACGCCACTATTTAATAGAGACCGCCACAACTGT

TAAATACCACTGGCGGTGGTACTGAGCACATCA-3'
|||||||||||||||||||||||||||||||||
ATTTATGGTGACCGCCACCATGACTCGTGTAGT-5';

5'-CATACAGATAACCATCTGCGGTGATAAATTATCTCTGGCGGTGTTGACA
   ||||||||||||||||||||||||||||||||||||||||||||||||
3'-GTATGTCTATTGGTAGACGCCACTATTTAATAGAGACCGCCACAACTGT

TAAATACCACTGGCGGTTATAATGAGCACATCA-3'
|||||||||||||||||||||||||||||||||
ATTTATGGTGACCGCCAATATTACTCGTGTAGT-5';

5'-CATACAGATAACCATCTGCGGTGATAAATTATCTCTGGCGGTGTTGACA
   ||||||||||||||||||||||||||||||||||||||||||||||||
3'-GTATGTCTATTGGTAGACGCCACTATTTAATAGAGACCGCCACAACTGT

TAAATACCACTGGCGATTATAATGAGCACATCA-3'
|||||||||||||||||||||||||||||||||
ATTTATGGTGACCGCTAATATTACTCGTGTAGT-5';

5'-CAAAAAATAAATTCATATAAAAAACATACAGTTAACCATCTGCGGTG
   |||||||||||||||||||||||||||||||||||||||||||||||
3'-GTTTTTTATTTAAGTATATTTTTTGTATGTCAATTGGTAGACGCCAC

ATAAATATTTATCTCTGGCGGTGTTGACATATACCACTGGCGGTGATATAATGA
|||||||||||||||||||||||||||||||||||||||||||||||||||||
TATTTATAAATAGAGACCGCCACAACTGTATATGGTGACCGCCACTATATTACT

GCACATCA-3'
||||||||
CGTGTAGT-5';

5'-CAAAAAATAAATTCATATAAAAAACATACAGTTATTTATCTCTGG
   |||||||||||||||||||||||||||||||||||||||||||||
3'-GTTTTTTATTTAAGTATATTTTTTGTATGTCAATAAATAGAGACC

CGGTGTTGACATAAATACCACTGGCGGTTATAATGAGCACATCA-3'
||||||||||||||||||||||||||||||||||||||||||||
GCCACAACTGTATTTATGGTGACCGCCAATATTACTCGTGTAGT-5'; and
``` wherein
A is deoxyadenyl;
G is deoxyguanyl;
C is deoxycytidyl;
T is thymidyl.

Single stranded deoxyoligonucleotides encoding both strands of the transcriptional activating sequences can be synthesized with commercially available instruments such as the 380B DNA synthesizer marketed by Applied Biosystems (850 Lincoln Center Dr., Foster City Calif. 94404), using β-cyanoethyl phosphoramidite chemistry. Other procedures for synthesizing DNA are also known in the art. The conventional modified phosphotriester method of synthesizing single stranded DNA is described by Itakura, et al., 1977, *Science* 198:1056 and by Crea, et al., 1978 *Proc. Nat. Acad. Sci. U.S.A.* 75:5765, and can also be used to synthesize the DNA encoding the transcriptional activating sequences of the present invention.

The transcriptional activating sequences of the present invention are derived from the bacteriophage lambda pL promoter-operator region (pL promoter). These activating sequences retain the highly desirable property of the pL promoter to be repressed by the lambda cI repressor protein. When a temperature sensitive cI repressor protein (cI857) is used in conjunction with the novel transcriptional activating sequences, transcription from the novel sequences is repressed at low temperatures (30° C.–35° C.), at which the cI repressor protein binds to the operator regions of the novel sequences and blocks transcription. At higher temperatures (37° C.–42° C.), the temperature sensitive cI repressor protein is disrupted and cannot block transcription from the transcriptional activating sequences. Thus, the novel sequences of the present invention retain the advantage of being regulatable in *Escherichia coli,* a characteristic that is highly desirable where large scale microbial fermentation is concerned.

In large scale fermentation cultures, the expression vectors of the present invention have the advantage of being more stable than expression vectors that contain the wild type lambda pL promoter-operator region. This increased structural stability can be attributed to the transcriptional activating sequences of the present invention which are shortened versions of the wild type bacteriophage lambda pL promoter. Thus, the present invention greatly decreases vector instability by eliminating DNA sequences which contribute to the instability. At the same time, the transcriptional activating sequences of the present invention maintain the ability to provide regulatable expression of an operably linked gene.

Preferred expression vectors of the present invention sequentially comprise a) one of the novel transcriptional activating sequences presented above,
b) a translational activating sequence, and
c) a DNA sequence that encodes a functional polypeptide, such that a) and b) are positioned for the expression of c).

In the expression vectors exemplified herein, the transcriptional activating sequences are linked to the translational activating sequences of the *Escherichia coli* lpp gene. A similar construction is disclosed and claimed in U.S. Pat. No. 4,874,703, issued Oct. 17, 1989, which is incorporated herein by reference. This patent discloses and claims the plasmid pL110, which comprises the wild type lambda pL promoter operator region linked to the *Escherichia coli* lpp gene translational activating sequence. In pL110 these activating sequences are operably linked to EK-BGH encoding DNA. The plasmids illustrated herein substitute the wild type pL promoter-operator region of pL110 with the novel transcriptional activating sequences of the present invention.

Preferred vectors of the present invention further comprise a selectable marker, a replicon that allows extrachromosomal maintenance of the vector and the temperature sensitive cI857 lambda repressor gene.

The plasmid pCZR125 is illustrative of the starting recombinant DNA vectors used in the construction of the recombinant DNA vectors of the present invention. This plasmid was constructed using plasmid pL110 as starting material. The plasmid pCZR125 was constructed by ligating the 5.8 kb XbaI-BamHI fragment of pL110 with two synthetic DNA fragments as described in Example 1. The synthetic DNA fragments encode an intact first cistron and the EK-BGH gene. pCZR125 provides two cistron production of EK-BGH. The two-cistron expression system is described by Schoner et al., 1986, *Proc. Natl. Acad. Sci. USA* 83:8506.

Upon large-scale culturing of cells containing the plasmid pCZR125 and subsequent analysis of the plasmid DNA from the culture, it was noted that pCZR125 displayed some structural instability. Analysis of vector stability is carried out by methods described in Example 8. A restriction site and function map of pCZR125 is presented in FIG. 1 of the accompanying drawings.

The plasmid pHPR97 was constructed to address the instability of pCZR125. pHPR97 was constructed by deleting the 418 base pair EcoRI-BglII restriction fragment from pCZR125 and ligating a synthetic DNA sequence that encoded the bacteriophage lambda pL promoter in its place. This promoter, which is also an element of the invention, was synthesized so as to contain EcoRI and BglII cohesive ends to provide for convenient cloning. The sequence of this DNA fragment is:

```
5'-AATTCGATCTCTCACCTACCAAACAATGCCCCCCTGCAAAAAATAAATTCAT
   |||||||||||||||||||||||||||||||||||||||||||||||||||
3'-GCTAGTGAGTGGATGGTTTGTTACGGGGGGACGTTTTTTATTTAAGTA

ATAAAAAACATACAGATAACCATCTGCGGTGATAAATTATCTCTGGCGGTGT
||||||||||||||||||||||||||||||||||||||||||||||||||||
TATTTTTTGTATGTCTATTGGTAGACGCCACTATTTAATAGAGACCGCCACA

TGACATAAATACCACTGGCGGTGATACTGAGCACATCA-3'
||||||||||||||||||||||||||||||||||||||
ACTGTATTTATGGTGACCGCCACTATGACTCGTGTAGTCTAG-5'
```

Thus, in pHPR97 the EK-BGH gene is operably linked to the above promoter sequence. Additionally, pHPR97 lacks 282 base pairs from the region originally present in plasmid pCZR125 located 5' to the wild type bacteriophage lambda pL promoter-operator sequence. The removal of this segment of DNA was found to have a positive effect on plasmid stability. Thus, the deletion of this region from the plasmid pCZR125 and pL110 are further embodiments contemplated by the present invention.

Figure 2:
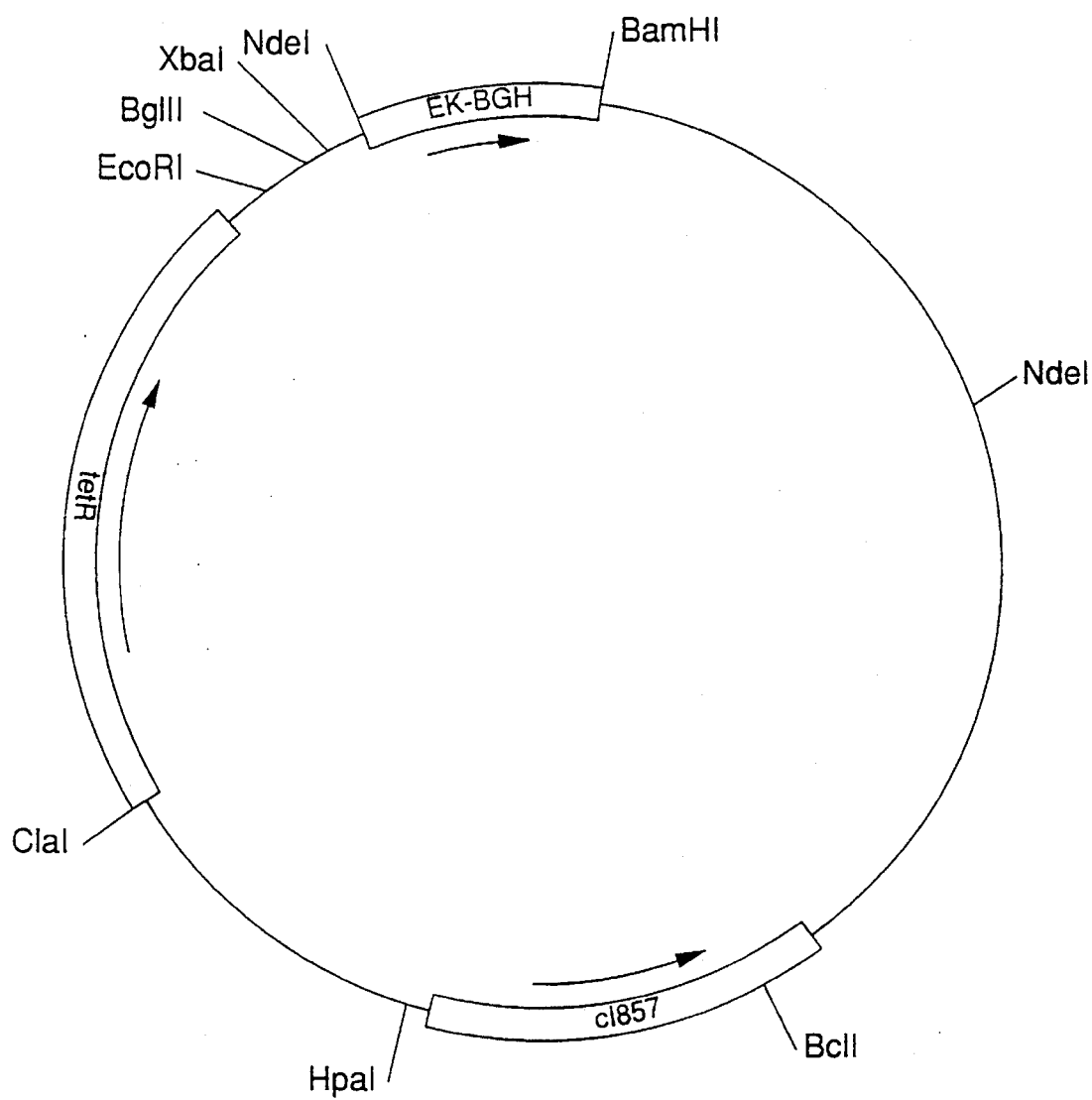
FIG. 2 is a restriction site and function map of plasmid pHPR97.

A restriction site and function map of pHPR97 is presented in FIG. 2 of the accompanying drawings.

The plasmid pHPR104 was constructed to address the plasmid instability of vectors that contained the wild type lambda promoter-operator region. Plasmid pHPR104 was constructed in a manner similar to pHPR97. The 6.0 kb EcoRI-BglII fragment of pCZR125 was ligated with a synthetic DNA segment that encoded a shortened derivative of the bacteriophage lambda pL promoter with EcoRI and BglII cohesive ends. The sequence of this DNA fragment is:

```
5'-AATTCATACAGATAACCATCTGCGGTGATAAATTATCTCTGGCGGTGTTGACA
   ||||||||||||||||||||||||||||||||||||||||||||||||||||
3'-GTATGTCTATTGGTAGACGCCACTATTTAATAGAGACCGCCACAACTGT

TAAATACCACTGGCGGTGATACTGAGCACATCA-3'
|||||||||||||||||||||||||||||||||
ATTTATGGTGACCGCCACTATGACTCGTGTAGTCTAG-5'.
```

This transcriptional activating sequence lacks 60 base pairs from the 5' region of the lambda pL promoter-operator region present in pHPR97. A restriction site and function map of pHPR104 is presented in FIG. 3 of the accompanying drawings.

The plasmid pHDM159 is constructed in a manner similar to pHPR104. The 6.0 kb EcoRI-BglII fragment of pCZR125 is ligated with a synthetic DNA fragment that encodes a derivative of the bacteriophage lambda pL promoter with EcoRI and BglII cohesive ends. The sequence of this DNA fragment is:

```
5'-AATTCATACAGATAACCATCTGCGGTGATAAATTATCTCTGGCGGTGTTGACA
    |||||||||||||||||||||||||||||||||||||||||||||||||||
  3'-GTATGTCTATTGGTAGACGCCACTATTTAATAGAGACCGCCACAACTGT

TAAATACCACTGGCGGTGGTACTGAGCACATCA-3'
|||||||||||||||||||||||||||||||||
ATTTATGGTGACCGCCACCATGACTCGTGTAGTCTAG-5'
```

This transcriptional activating sequence is the same as that present in pHPR104 except that a G is substituted for the A located 72 bases from the 5' end of the DNA fragment. This change was made based on the findings of Sarai & Tukeda, 1989, *Proc. Natl. Acad. Sci.* 86:6513. As described by Sarai and Tukeda, the corresponding base substitution in the $O_R1$ repressor binding site results in a promoter-operator region that is more tightly regulated than the wild type lambda promoter. The corresponding change in $O_L1$ was expected to have the same effect. A restriction site and function map of pHDM159 is presented in FIG. 4 of the accompanying drawings.

The plasmid pHPR106 was constructed in a manner similar to the plasmids above. The 6.0 kb EcoRI-BglII fragment of pCZR125 was ligated with a synthetic DNA fragment that encoded a derivative of the bacteriophage lambda pL promoter with EcoRI and BglII cohesive ends. The sequence of this DNA fragment is:

```
5'-AATTCATACAGATAACCATCTGCGGTGATAAATTATCTCTGGCGGTGTTGACA
    |||||||||||||||||||||||||||||||||||||||||||||||||||
  3'-GTATGTCTATTGGTAGACGCCACTATTTAATAGAGACCGCCACAACTGT

TAAATACCACTGGCGGTTATAATGAGCACATCA-3'
|||||||||||||||||||||||||||||||||
ATTTATGGTGACCGCCAATATTACTCGTGTAGTAG-5'.
```

This transcriptional activating sequence is identical to that of pHPR104 except that it has been constructed to contain a −10 consensus sequence. The wild type lambda promoter-operator region does not contain a −10 consensus sequence. This sequence was added to the transcriptional activating sequence of pHPR106 because of the well known effect that a −10 consensus can increase the expression of an operably linked gene. A surprising aspect of this transcriptional activating sequence is that although the altered −10 sequence is in the region that binds the lambda repressor protein, regulation of the promoter is maintained. A restriction site and function map of pHPR106 is presented in FIG. 5 of the accompanying drawings.

The plasmid pHPR106A was constructed in the manner described for plasmid pHPR106. However, the sequence of the synthetic DNA fragment encoding the derivative of the bacteriophage lambda pL promoter is:

```
5'-CATACAGATAACCATCTGCGGTGATAAATTATCTCTGGCGGTGTTGACA
   |||||||||||||||||||||||||||||||||||||||||||||||||
 3'-GTATGTCTATTGGTAGACGCCACTATTTAATAGAGACCGCCACAACTGT

TAAATACCACTGGCGATTATAATGAGCACATCA-3'
|||||||||||||||||||||||||||||||||
ATTTATGGTGACCGCTAATATTACTCGTGTAGT-5';
```

This transcriptional activating sequence is identical to that present in pHPR106 except that the G at position 65 (reading from the 5' end of the top strand) was converted to an A. The restriction site and function map of pHPR106A is identical to that presented in FIG. 5.

The plasmid psyn3 was constructed by the method presented in Example 6. The 6.3 kb EcoRI-BglII fragment of plasmid pLl10 was ligated with a synthetic DNA fragment that encoded a derivative of the bacteriophage lambda pL promoter with EcoRI and BglII cohesive ends. The sequence of this DNA fragment is:

```
5'-AATTCAAAAAATAAATTCATATAAAAAACATACAGTTAACCATCTGCGGTG
   ||||||||||||||||||||||||||||||||||||||||||||||||||
   3'-GTTTTTTATTTAAGTATATTTTTGTATGTCAATTGGTAGACGCCAC

ATAAATATTTATCTCTGGCGGTGTTGACATATACCACTGGCGGTGATATAATGA
||||||||||||||||||||||||||||||||||||||||||||||||||||||
TATTTATAAATAGAGACCGCCACAACTGTATATGGTGACCGCCACTATATTACT

GCACATCA-3'
||||||||
CGTGTAGTCTAG-5'.
```

Figure 6:
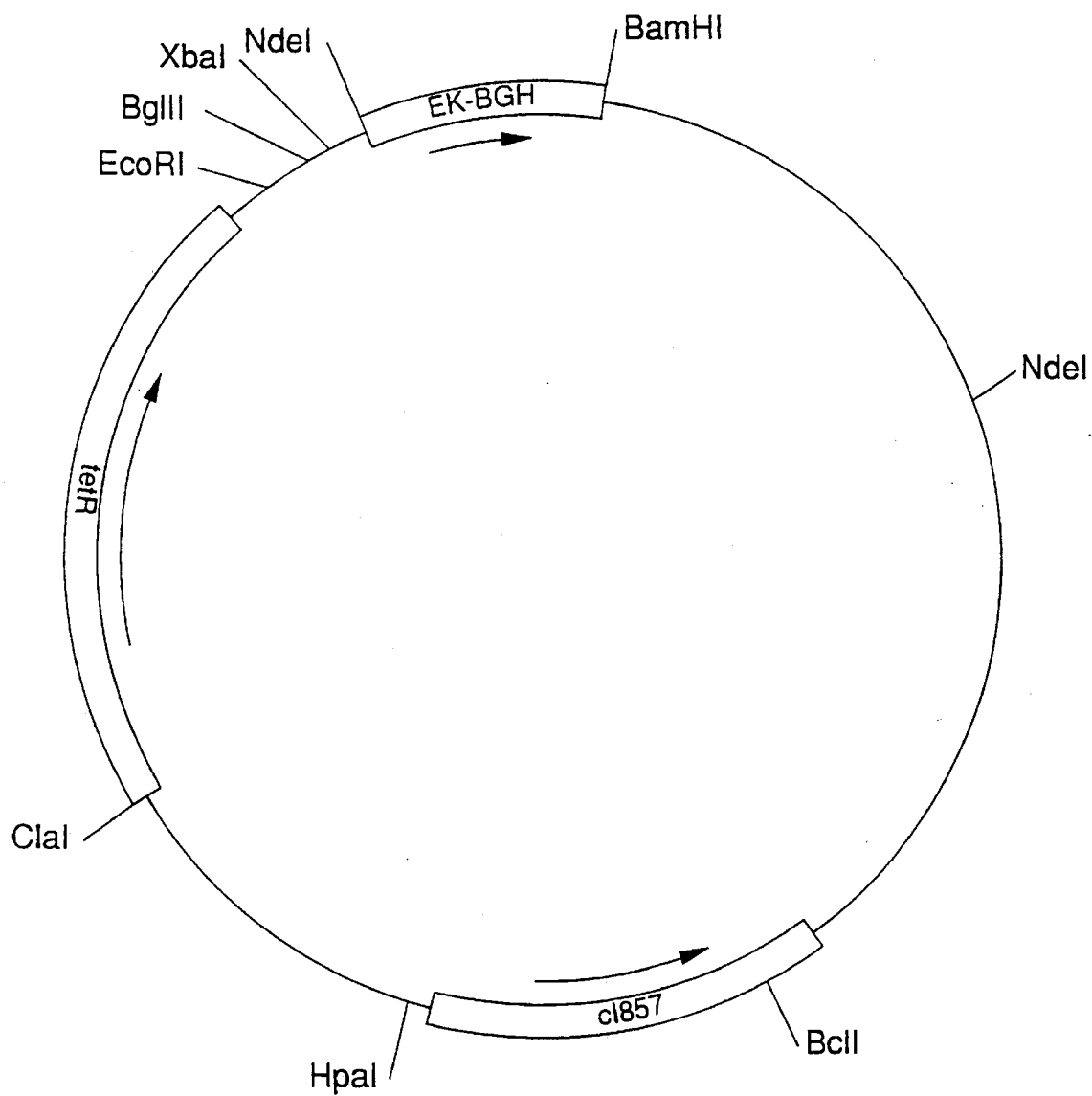
FIG. 6 is a restriction site and function map of plasmid psynC.

Preferably, the synthetic DNA fragment of psyn3 is ligated into the 6.0 kb EcoRI-BglII fragment of pCZR125 to create the plasmid psynC. A restriction site and function map of psynC is presented in FIG. 6 of the accompanying drawings.

The plasmid psyn4 was constructed by the method presented in Example 8. This plasmid was constructed in order to eliminate the $O_L3$ operator region from the transcriptional activating sequence of plasmid psyn3. A preferred vector that provides a transcriptional activating sequence identical to that of psyn4 is plasmid psynD. To construct psynD, the 6.0 Kb EcoRI-BglII fragment of pCZR125 is ligated with a synthetic DNA fragment that encodes the derivative of the bacteriophage lambda pL promoter present in psyn4. The sequence of this DNA fragment is:

```
5'-AATTCAAAAAATAAATTCATATAAAAAACATACAGTTATTTATCTCTGG
   |||||||||||||||||||||||||||||||||||||||||||||||||
   3'-GTTTTTTATTTAAGTATATTTTTGTATGTCAATAAATAGAGACC

CGGTGTTGACATAAATACCACTGGCGGTTATAATGAGCACATCA-3'
||||||||||||||||||||||||||||||||||||||||||||
GCCACAACTGTATTTATGGTGACCGCCAATATTACTCGTGTAGTCTAG-5'.
```

Figure 7:
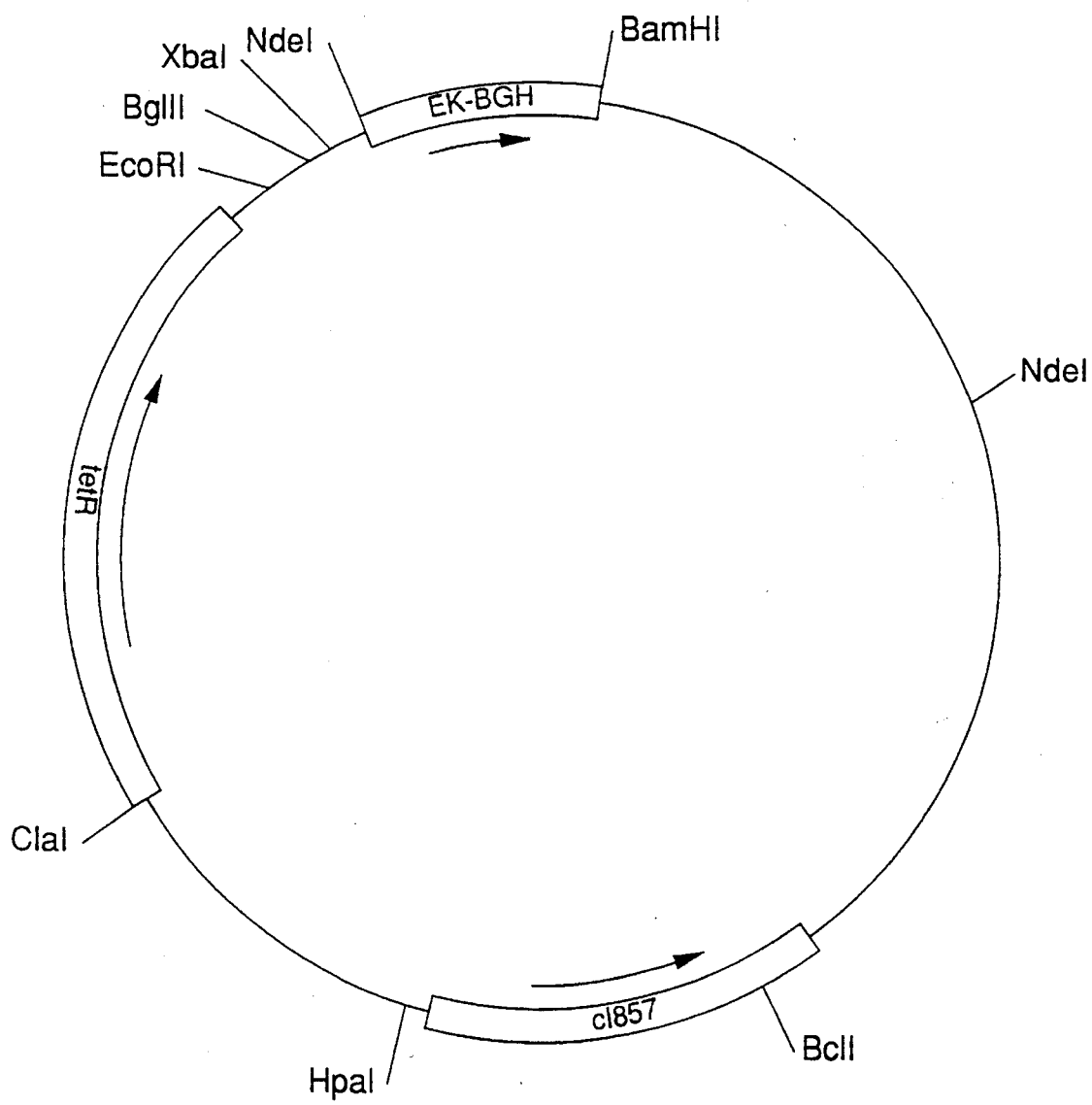
FIG. 7 is a restriction site and function map of plasmid psynD.

A restriction site and function map of psynD is presented in FIG. 7 of the accompanying drawings.

Plasmids pHPR97, pHPR104, pHDM159, pHPR106, pHPR106A, psyn3, psynC, psyn4 and psynD are useful, regulatable expression vectors. A variety of functional polypeptide-encoding DNA fragments can be introduced into and expressed from these plasmids. The functional polypeptide-encoding DNA can be introduced into these plasmids on an XbaI-BamHI or a NdeI-BamHI restriction fragment, in a reaction that replaces the corresponding XbaI-BamHI or NdeI-BamHI fragment containing the EK-BGH encoding DNA of these plasmids with the functional polypeptide-encoding DNA desired to be expressed. The modifications necessary to convert a functional polypeptide-encoding DNA into the required XbaI-BamHI or NdeI-BamHI restriction fragment employ reactions within the capacity of one skilled in the art. Other polypeptide-encoding DNA that can be introduced into the expression vectors of the present invention include, for example: β-galactosidase, human pre-proinsulin, human proinsulin, human insulin A-chain, human insulin B-chain, non-human insulin, human growth hormone, insulin-like growth factors, human interferon, viral antigens, urokinase, tissue-type plasminogen activator, interleukins 1–6, colony stimulating factors, erythropoetin, human transferrin and the like.

Also, the expression vectors of the present invention preferrably contain a translational activating sequence. Translational activating sequences are discussed by Shine and Dalgarno, 1975, *Nature* 254:34 and Steitz, J. A., in *Biological Regulation and Development: Gene Expression* 1:349 (ed. R. F. Goldberg, 1979). Methods for cloning translational activating sequences are described by Maniatis et al., *Molecular Cloning: A Laboratory Manual,* Cold Spring Harbor Laboratory Press, Cold Spring Harbor, N.Y. (2d ed. 1989).

The present transcriptional activating sequences have EcoRI and BglII cohesive ends located at the ends of the molecule. The cohesive ends were used to facilitate the cloning of the transcriptional activating sequence into the cloning vectors illustrated herein. These cohesive ends facilitate ligation but do not contribute to the activity of the sequences. The skilled artisan will recognize that these ends can be altered, or the entire transcriptional activating sequences constructed to facilitate ligation into restriction enzyme recognition sites other than EcoRI or BglII. Therefore, the present invention is in no way limited to the exact DNA sequences specifically exemplified.

The plasmids psyn3, psynC, psyn4, psynD, pHPR106, pHPR106A and pHDM159 contain transcriptional activating sequences wherein the DNA sequence has been significantly changed. The transcriptional activating sequences of psynC and psyn3 contain a −10 consensus sequence and alterations in the first repressor binding region. The transcriptional activating sequences of psynD and psyn3 have been altered such that the $O_L3$ operator region has been eliminated. The transcriptional activating sequences of pHPR106 and pHPR106A contain a −10 consensus sequence with a single base alteration in the $O_L1$ repressor binding region. This alteration results in enhanced transcriptional activating activity with a minimum effect on repressor binding and repressability. pHDM159 contains a change that increases the binding affinity for the cI857 repressor. pHDM159 was constructed with a single base change in the −10 region so that it would have a minimal effect on the transcriptional activating activity. Thus, the present invention includes a variety of modified bacteriophage lambda pL promoter-operator regions which provide for increased vector stability while providing regulated expression of an operably linked gene.

Those skilled in the art will recognize that the present invention also provides a method wherein a functional polypeptide product is expressed from the host cell that contains the recombinant DNA expression vectors presented herein using appropriate fermentation conditions. Upon completion of fermentation, the heterologous polypeptide product is isolated from the host cell or the resulting fermentation broth by a variety of methods known in the art. The present invention can be practiced in both defined and complex media formulations. Those skilled in the art recognize that the medium used in a fermentation process is critical to maximizing product expression. A variety of media including, for example, those discussed in Maniatis et al., 1982, should be evaluated to determine the best medium for the particular expression system used in practicing the present invention. For example, a medium formulation such as that described by Domach et al., 1984, *Biotechnology and Bioengineering,* vol. XXVI:203–206 can be used as the fermentation media for growth of the transformed cells of the present invention. The transformants are cultured under conditions suitable for growth until numbers sufficient for optimal expression are obtained. At this time the temperature of the culture can be raised to a level that will inactivate the temperature sensitive cI857 repressor gene product and, thus, allow the expression from the novel transcriptional activating sequences to occur.

The following examples are intended to assist in further understanding of the invention. Particular materials employed, species, and conditions are intended to be further illustrative of the invention and not limiting the reasonable scope thereof. All enzymes referred to in the examples are available, unless otherwise indicated, from Bethesda Research Laboratories (BRL), Gaithersburg, Md. 20877 or New England Biolabs Inc. (NEB), Beverly, Mass. 01915, or Boehringer-Mannheim Biochemicals, 7941 Castleway Drive, P.O. Box 50816, Indianapolis, Ind. 46250 and are used in substantial accordance with the manufacturer's recommendations.

EXAMPLE 1

Construction of pCZR125

A. Preparation of the 5.8kb XbaI-BamHI Restriction Fragment of pL110

Twenty-five µg of plasmid pL110 was digested to completion with 15 µl (150 units) of XbaI in a 500 µl reaction volume containing 60 mM Tris-HCl (pH 7.5) (Tris is Tris [hydroxymethyl]aminomethane), 10 mM $MgCl_2$, 100 mM $NaCl_2$ and 1 mM β-mercaptoethanol. The mixture was incubated at 37° C. for one hour. The digested DNA was extracted two times with a mixture of phenol and chloroform (50:50) and the aqueous layer was recovered. The DNA was recovered from the aqueous layer by addition of 2.5 volumes of absolute ethanol and 0.1 volume of 3M sodium acetate. The DNA was collected by centrifugation and was resuspended in 50 µl of water.

The above DNA was partially digested with BamHI as follows. Fifty µl of the XbaI-digested DNA was mixed with 0.2 µl (2 units) of BamHI in a 150 µl reaction volume consisting of 10 mM Tris-HCl (pH 7.8), 7 mM $MgCl_2$, 150 mM NaCl, and 6 mM β-mercaptoethanol. The mixture was incubated at 37° C. for 5 minutes. The sample was purified and recovered as described above and resuspended in 50 µl of TE (TE is 10 mM Tris-HCl (pH 7.4) and 1 mM ethylenediaminetetra-acetic acid (EDTA)). Five µl of loading buffer (25% v/v glycerol, 0.05% w/v bromphenol blue, and 0.5% w/v xylene cyanole) was added to the sample and the digested DNA was fractionated on a 1% agarose gel by gel electrophoresis as described by Maniatis et al. at pages 150–172 (Maniatis et al., 1982, *Molecular Cloning: a Laboratory Manual,* Cold Spring Harbor Laboratory, Cold Spring Harbor, N.Y.). The agarose gel was stained with a dilute solution of ethidium bromide and the 5.8 kb XbaI-BamHI restriction fragment was visualized under a 300 nm UV light. The portion of the gel containing this restriction fragment was recovered. The DNA was purified by mincing the gel slice, extracting twice with phenol:chloroform (50:50) and ethanol precipitating the DNA as described above.

B. Preparation of XbaI-NdeI linker

The following complementary DNA segments were synthesized on an automated DNA synthesizer (Applied Biosystems 380B) using β-cyanoethyl phosphoramidite chemistry:

1. 5'-CTAGAGGGTATTAATAATGTATAT-TGATTTTAATAAGGA GGAATAATCA-3'
2. 5'-TATGATTATTCCTCCTTATTAAAAT-CAATATACATTATT AATACCCT-3'.

These single stranded DNA segments were conventionally purified and resuspended in water.

Five µg of each single stranded DNA segment was mixed and heated to 70° C. for five minutes. The mixture was cooled at room temperature for 30 minutes to allow the DNA segments to anneal.

The annealed DNA fragment was treated with 1 µl (10 units) of T4 polynucleotide kinase in 70 mM Tris-HCl (pH 7.6), 0.1 M KCl, 10 mM $MgCl_2$, 5 mMDTT containing 0.2 mM deoxyadenine 5'-triphosphate in a total volume of 20 µl. The mixture was incubated at 37° C. for thirty minutes. The mixture was then incubated at 70° C. for 5 minutes and then cooled at room temperature.

C. Preparation of the Synthetic EK-BGH gene

The DNA fragment encoding the EK-BGH gene was synthesized in substantial accordance with the method of Example 1B. The gene encoding EK-BGH was constructed from 16 chemically synthesized pieces of single stranded DNA, ranging from 71 to 83 nucleotides in length, which, when annealled, comprise both complementary strands of the EK-BGH gene with NdeI-BamHI cohesive ends. The sequence of the synthetic EK-BGH gene is:

```
5'-TATGTTCCCATTGGATGATGATGATAAGTTCCCAGCCATGTCCTT
   ||||||||||||||||||||||||||||||||||||||||||||||
3'-ACAAGGGTAACCTACTACTACTATTCAAGGGTCGGTACAGGAA

GTCCGGCCTGTTTGCCAACGCTGTGCTCCGGGCTCAGCACCTGCATCAGCTGGCTGCTGA
||||||||||||||||||||||||||||||||||||||||||||||||||||||||||||
CAGGCCGGACAAACGGTTGCGACACGAGGCCCGAGTCGTGGACGTAGTCGACCGACGACT

CACCTTCAAAGAGTTTGAGCGCACCTACATCCCGGAGGGACAGAGATACTCCATCCAGAA
||||||||||||||||||||||||||||||||||||||||||||||||||||||||||||
GTGGAAGTTTCTCAAACTCGCGTGGATGTAGGGCCTCCCTGTCTCTATGAGGTAGGTCTT

CACCCAGGTTGCCTTCTGCTTCTCTGAAACCATCCCGGCCCCCACGGGCAAGAATGAGGC
||||||||||||||||||||||||||||||||||||||||||||||||||||||||||||
GTGGGTCCAACGGAAGACGAAGAGACTTTGGTAGGGCCGGGGGTGCCCGTTCTTACTCCG
```

-continued

```
CCAGCAGAAATCAGACTTGGAGCTGCTTCGCATCTCACTGCTCCTCATCCAGTCGTGGCT
||||||||||||||||||||||||||||||||||||||||||||||||||||||||||||
GGTCGTCTTTAGTCTGAACCTCGACGAAGCGTAGAGTGACGAGGAGTAGGTCAGCACCGA

TGGGCCCCTGCAGTTCCTCAGCAGAGTCTTCACCAACAGCTTGGTGTTTGGCACCTCGGA
||||||||||||||||||||||||||||||||||||||||||||||||||||||||||||
ACCCGGGGACGTCAAGGAGTCGTCTCAGAAGTGGTTGTCGAACCACAAACCGTGGAGCCT

CCGTGTCTATGAGAAGCTGAAGGACCTGGAGGAAGGCATCCTGGCCCTGATGCGGGAGCT
||||||||||||||||||||||||||||||||||||||||||||||||||||||||||||
GGCACAGATACTCTTCGACTTCCTGGACCTCCTTCCGTAGGACCGGGACTACGCCCTCGA

GGAAGATGGCACCCCCGGGCTGGGCAGATCCTCAAGCAGACCTATGACAAATTTGACAC
||||||||||||||||||||||||||||||||||||||||||||||||||||||||||||
CCTTCTACCGTGGGGGCCCGACCCGTCTAGGAGTTCGTCTGGATACTGTTTAAACTGTG

AAACATGCGCAGTGACGACGCGCTGCTCAAGAACTACGGTCTGCTCTCCTGCTTCCGGAA
||||||||||||||||||||||||||||||||||||||||||||||||||||||||||||
TTTGTACGCGTCACTGCTGCGCGACGAGTTCTTGATGCCAGACGAGAGGACGAAGGCCTT

GGACCTGCATAAGACGGAGACGTACCTGAGGGTCATGAAGTGCCGCCGCTTCGGGGAGGC
||||||||||||||||||||||||||||||||||||||||||||||||||||||||||||
CCTGGACGTATTCTGCCTCTGCATGGACTCCCAGTACTTCACGGCGGCGAAGCCCCTCCG

CAGCTGTGCCTTCTAG-3'
||||||||||||||||
GTCGACACGGAAGATCCTAG-5'
```

D. DNA Ligation

Two μl (0.2 pg) of the pL110 restriction fragment prepared in Example 1A, 2 μl (8.75 pmoles) of the DNA fragment prepared in Example 1B, and 2 μl (0.1 μg) of the DNA fragment prepared in Example 1C were ligated in a reaction containing 1 M μl (10 units) of T4 DNA ligase, 50 mM Tris-HCl (pH 7.6), 10 mMMgCl$_2$, 1 mM dithiothreitol, 1 mM of adenine 5'-triphosphate and 5% (w/v) polyethylene glycol-8000 in a total volume of 10 μl. The mixture was incubated at 16° for 16 hours. A portion of this mixture was used to transform *Escherichia coli* cells as described below.

E. Transformation Procedure

*Escherichia coli* K12 RV308 cells are available from the Northern Regional Research Laboratory, Peoria, Ill. under the accession number NRRL B-15624. A 50 ml culture of *E. coli* K12 RV308 was grown in L-broth (10 g tryptone, 10 g NaCl and 5 g yeast extract per liter of H$_2$O) to an O.D.$_{590}$ of 0.5 absorbance units. The culture was chilled on ice for ten minutes and then the cells were collected by centrifugation. The cell pellet was resuspended in 25 ml of cold 50 mM CaCl$_2$:10 mM Tris-HCl (pH 8.0) and incubated on ice for 15 minutes. The cells were collected by centrifugation, the cell pellet was resuspended in 2.5 ml of cold 50 mM CaCl$_2$:10mM Tris-HCl (pH 8.0) and the sample was held at 4° C. for 16 hours.

Two hundred μof this cell suspension was mixed with 50 μl of the ligated DNA prepared above and then incubated on ice for 60 minutes. The mixture was incubated at 32° C. for 45 seconds and then placed on ice for 2 minutes. Five ml of TY medium (1% tryptone, 0.5% yeast extract and 1% sodium chloride, pH 7.4) was added to the mixture and incubation was continued at 32° C. for 2 hours. One hundred μl of this culture was spread on TY agar plates (1% tryptone, 0.5% yeast extract, 1% sodium chloride and 1.5% agar at pH 7.4) that contained 5 μg/ml of tetracycline. These plates were incubated 16 hours at 32° C. The tetracycline resistant colonies were individually picked and used to inoculate 2 ml of TY medium. The cultures were incubated at 37° C. with aeration for 16 hours.

F. DNA Isolation Procedure

Plasmid DNA was isolated from the culture of transformants as follows. All of the following manipulations were done at ambient temperature unless otherwise indicated. One and a half ml of each of the cultures was transferred to a microcentrifuge tube. The cells were collected by a 1 minute centrifugation. The supernatant was removed with a fine-tip aspirator and the cell pellet was suspended in 100 μl of a solution containing 50 mM glucose, 10 mM EDTA and 25 mM Tris-HCl (pH 8.0). After incubation at room temperature for 5 minutes, 200 μl of an alkaline sodium dodecyl sulfate (SDS) solution (0.2N NaOH, 1% SDS) was added. The tube was gently inverted to mix and then maintained on ice for 5 minutes. Next, 150 μl of a potassium acetate solution (prepared by adding 11.5 ml of glacial acetic acid and 28.5 ml of water to 60 ml of 5M potassium acetate. The resulting solution is 3M with respect to potassium and 5M with respect to acetate) was added and the contents of the tube mixed by gently vortexing. The sample was kept on ice for 5 minutes and then centrifuged for 10 minutes. The supernatant was transferred to a second centrifuge tube to which an equal volume of phenol (saturated with 0.1M Tris (pH 8.0)) was added. The sample was mixed and then centrifuged for 5 minutes. The supernatant was collected and the phenol extraction was repeated. One ml of ice-cold absolute ethanol was added to the supernatant. The sample was mixed and held on dry ice until highly viscous, but not frozen solid. The DNA was then collected by a 5 minute centrifugation. The supernatant was removed by aspiration and 500 μl of 70% ethanol was added to the DNA pellet. The sample was gently vortexed to wash the pellet and centrifuged for 2 minutes. The supernatant was removed and the DNA pellet was dried under vacuum. The DNA was dissolved in 50 μl of TE (10 mM Tris-HCl (pH 8.0) and 1 mM EDTA) and stored at 4° C.

G. Large Scale DNA Isolation

Large amounts of pCZR125 plasmid DNA were isolated as follows. One liter of L broth containing 5 μg/ml tetracycline was inoculated with a colony of *Escherichia coli* RV308/pCZR125. The culture was grown at 32° C. for 16 hours. The culture was centrifuged in a GSA rotor (Sorvall) at 6000 rpm for 5 minutes at 4° C. The resulting supernatant was discarded, and the cell pellet was washed in 40 ml of TES buffer (10 mM Tris-HCl (pH 7.5), 10 mM NaCl, and 1 mM EDTA) and then collected by centrifugation. The supernatant was discarded, and the cell pellet was frozen in a dry ice-ethanol bath and then thawed. The thawed cell pellet was resuspended in 10 ml of a solution of 25% sucrose and 50 mM EDTA. One ml of a 5 mg/ml lysozyme solution, 3 ml of 0.25M EDTA (pH 8.0), and 100 μl of 10 mg/ml boiled RNAse A (available from Sigma Chemical Co., P.O. Box 14508, St. Louis, Mo.) were added to the solution, which was then incubated on ice for 15 minutes. Three ml of lysing solution (prepared by mixing 3 ml of 10% Triton X-100, 75 ml of 0.25M EDTA (pH 8.0), 15 ml of 1M Tris-HCl (pH 8.0), and 7 ml of $H_2O$) were added to the lysozyme treated cells, mixed, and the resulting solution incubated on ice for another 15 minutes. The lysed cells were frozen in a dry ice-ethanol bath and then thawed.

The cellular debris was removed from the solution by centrifugation at 25,000 rpm for 40 minutes in a SW28.1 rotor (Beckman, Scientific Instrument Division, Campus Drive at Jamboree Blvd., Irvine, Calif. 92713) and by extraction with buffered phenol. About 30.44 g of CsCl and ~1 ml of a 5 mg/ml ethidium bromide solution were added to the cell extract, and then the volume of the solution was adjusted to 40 ml with TES buffer (10 mM Tris-HCl (pH 7.5), 10 mM NaCl and 1 mM EDTA). The solution was decanted into a VTi50 ultracentrifuge tube (Beckman), which was then sealed and centrifuged in a VTi50 rotor at 42,000 rpm for about 16 hours. The resulting plasmid band, visualized with ultraviolet light, was isolated and then placed in a Ti75 tube and rotor (Beckman) and centrifuged at 50,000 rpm for 16 hours. Any necessary volume adjustments were made using TES containing 0.761 g/ml CsCl. The plasmid band was again isolated, extracted with salt-saturated isopropanol to remove the ethidium bromide, and diluted 1:3 with TES buffer. One volume of 3M sodium acetate and two volumes of absolute ethanol were then added to the solution, which was then incubated for 16 hours at $-20°$ C. The plasmid DNA was pelleted by centrifuging the solution in an SS34 rotor (Sorvall) for 15 minutes at 10,000 rpm. The plasmid DNA obtained by this procedure was suspended in TE buffer and stored at $-20°$ C.

EXAMPLE 2

Construction of pHPR97

A. Preparation of EcoRI-BglII Digested pCZR125

Ten μg of pCZR125 DNA was digested to completion with 5 μl (55 units) of EcoRI and 5 μl (55 units) of BglII in a 60 μl reaction volume containing 10 mM Tris-HCl (pH 7.5), 100 mMNaCl, 10 mMMgCl$_2$, and 10 mM β-mercaptoethanol. The reaction was incubated at 37° C. for two hours. The digested DNA was purified and the 6.0 kb fragment was isolated by preparative agarose gel electrophoresis as described in Example 1A.

B. Preparation of the Transcriptional Activating Sequence DNA

A transcriptional activating sequence was prepared by synthesizing the following single stranded DNA sequences:
1. 5'-AATTCGATCTCTCACCTACCAAACAATGCCCCCCTGCAAA AAATAAATTCATATAAAAAACATACAGATAACCATCTGCGGTGATAAATTATCTCTGGCGGTGTTGACATAAATACCACT GGCGGTGATACTGAGCACATCA-3'
2. 5'-GATCTGATGTGCTCAGTATCACCGCCAGTGGTATTTATGT CAACACCGCCAGAGATAATTTATCACCGCAGATGGTTATCTGTATGTTTTTTATATGAATTTATTTTTTGCAGGGGGGCA TTGTTTGGTAGGTGAGAGATCG-3'

These single stranded DNA segments were synthesized on an automated DNA synthesizer (Applied Biosystems 380B) using β-cyanoethyl phosphoramidite chemistry. The synthetic DNA segments were purified and then stored in TE buffer at 0° C.

Ten μl (5 μg) of each single stranded DNA segment was mixed and heated to 70° C. for 5 minutes. The mixture was cooled at room temperature for 30 minutes to allow the DNA segments to anneal.

The annealed DNA fragment was treated with 1 μl (10 units) of T4 polynucleotide kinase in 70 mM Tris-HCl (pH 7.6), 0.1M KCl, 10 mM MgCl$_2$, 5 mMDTT containing 0.2 mM adenine 5'-triphosphate in a total volume of 20 μl. The mixture was incubated at 37° C. for thirty minutes. The mixture was then incubated at 70° C. for 5 minutes and then cooled at room temperature.

C. Final Construction of pHPR97

Two μg of the restriction fragment prepared in Example 2A and 1 μg of the kinased DNA fragment prepared in Example 2B were ligated in substantial accordance with the method of Example 1D, except that the mixture was incubated at room temperature for 1 hour, heated to 70° C. for 5 minutes and then cooled to room temperature. A portion of the ligated DNA was used to transform *Escherichia coli* K12 MM294 cells according to the method of Example 1E. *E. coli* K12 MM294 cells are available from the American Type Culture Collection, Rockville, Md. 20852 under accession number ATCC 31446. Tetracycline resistant transformants were selected and their plasmid DNA was isolated according to the alkaline lysis method described in Example 1F. Restriction analysis was performed to confirm the structure of pHPR97. A restriction site and function map of pHPR97 is presented in FIG. 2.

EXAMPLE 3

Construction of pHPR104

The plasmid pHPR104 was constructed in substantial accordance with Example 2. However, the synthetic transcriptional activating sequence was constructed from the following single stranded DNA segments:
1. 5'-AATTCATACAGATAACCATCTGCGGTGATAAATTATCTC TGGCGGTGTTGACATAAATACCACTGGCGGTGATACTGAGCA CATCA-3'
2. 5'-GATCTGATGTGCTCAGTATCACCGCCAGTGGTATTTATG TCAACACCGCCAGAGATAATTTATCACCGCAGATGGTTATCT GTATG-3'.

Figure 3:
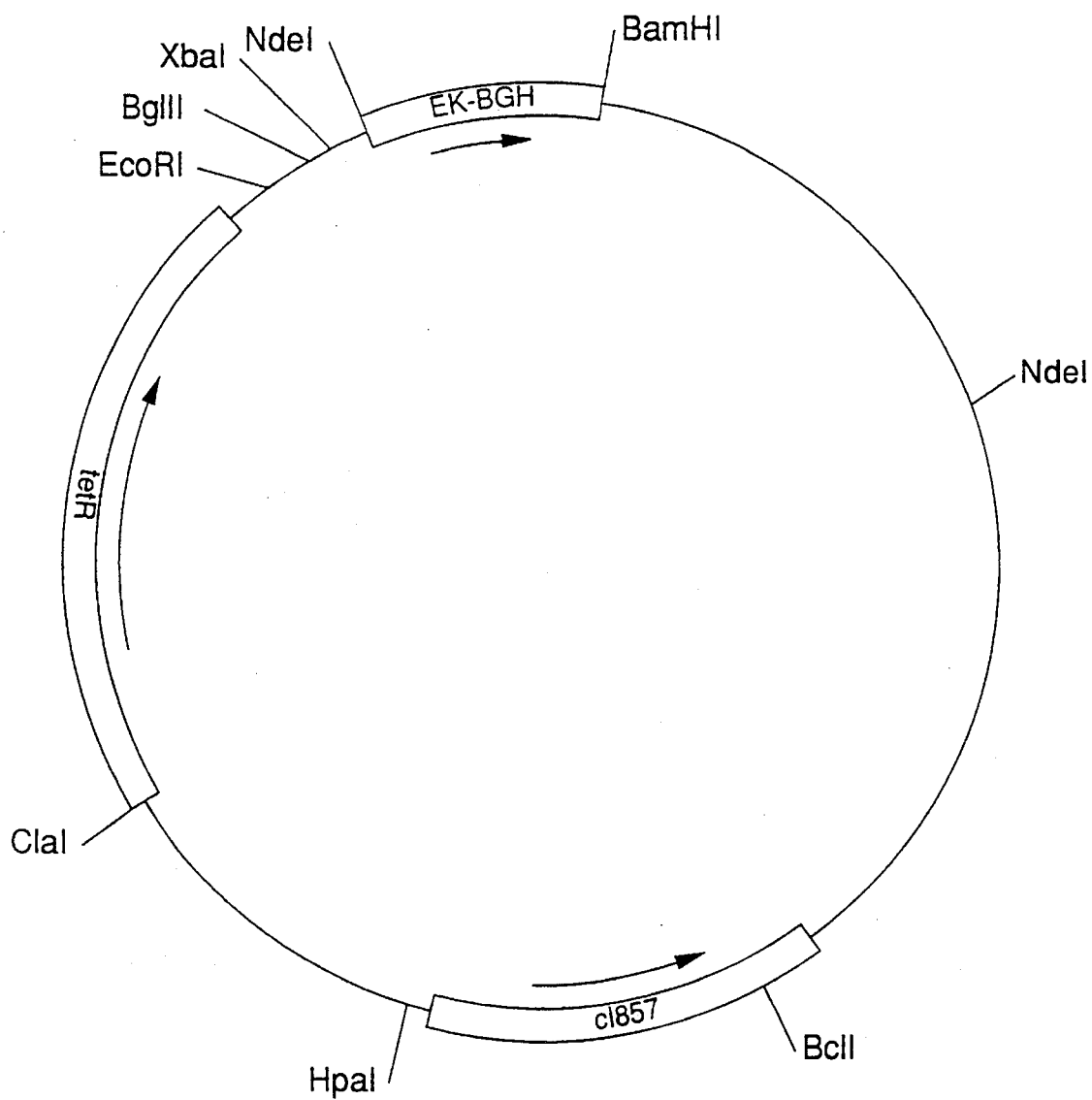
FIG. 3 is a restriction site and function map of plasmid pHPR104.

A restriction site and function map of pHPR104 is presented in FIG. 3.

EXAMPLE 4

Construction of pHDM159

The plasmid pHDM159 is constructed in substantial accordance with Example 2. However, the synthetic transcriptional activating sequence is constructed from the following single stranded DNA segments:
1. 5'-AATTCATACAGATAACCATCTGCGGTGATAAATTATCTC TGGCGGTGTTGACATAAATACCACTGGCGGTGGTACTGAGCA CATCA-3'
2. 5'-GATCTGATGTGCTCAGTACCACCGCCAGTGGTATTTATG TCAACACCGCCA-

GAGATAATTTATCACCGCAGATGGTTATCTGTATG-3'.

Figure 4:
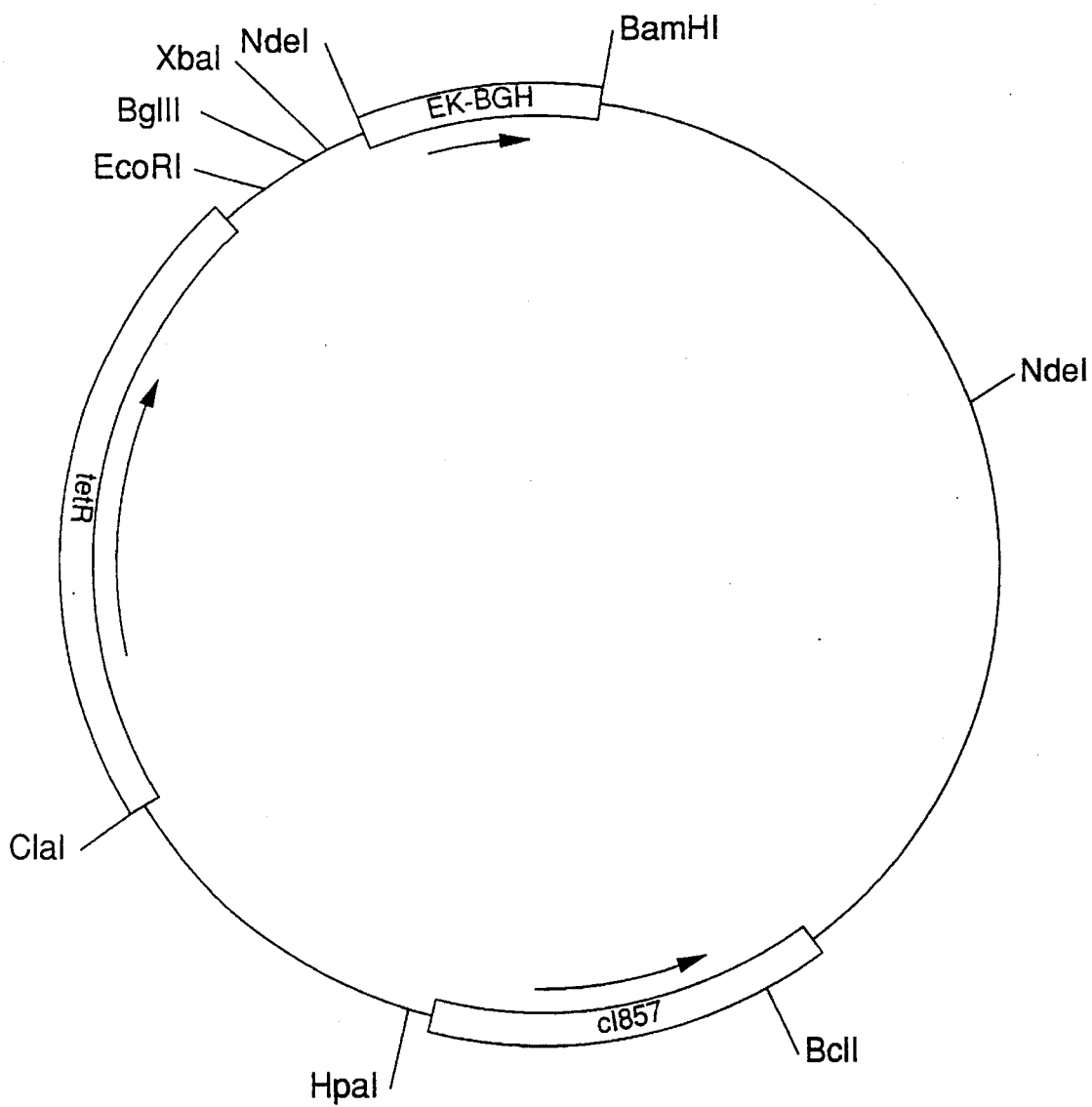
FIG. 4 is a restriction site and function map of plasmid pHDM159.

A restriction site and function map of pHDM159 is presented in FIG. 4.

EXAMPLE 5

Construction of pHPR106

The plasmid pHPR106 was constructed in substantial accordance with Example 2. However, the synthetic transcriptional activating sequence was constructed from the following single stranded DNA segments:

1. 5'-AATTCATACAGATAACCATCTGCGGTGATAAATTATCTCTGG CGGTGTTGACATAAATACCACTGGCGGTTATAATGAGCACATCA-3'
2. 5'-GATCTGATGTGCTCATTATAACCGCCAGTGGTATTTATGTCAA CACCGCCAGAGATAATTTATCACCGCAGATGGTTATCTGTATG-3'.

Figure 5:
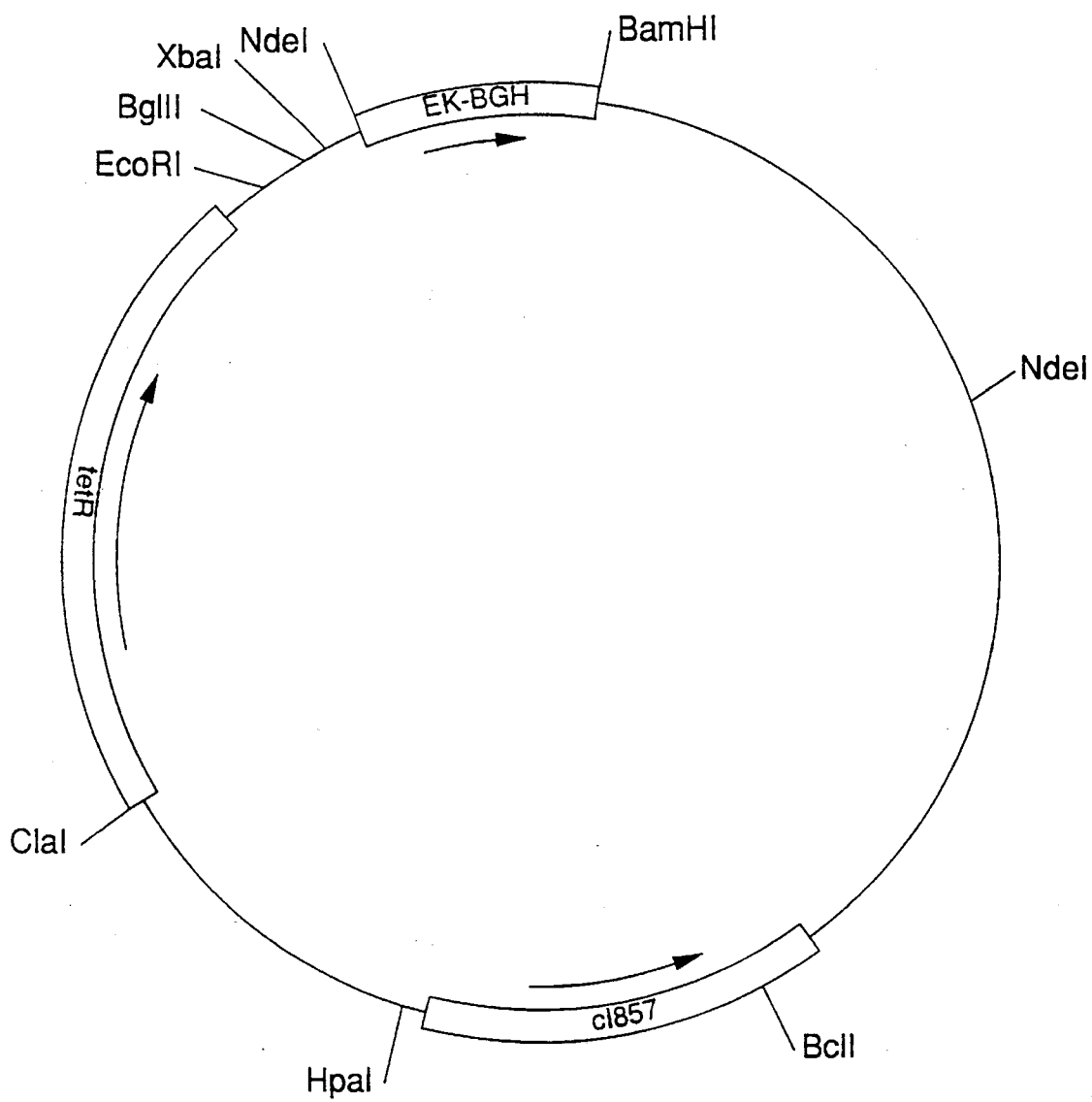
FIG. 5 is a restriction site and function map of plasmid pHPR106.

A restriction site and function map of pHPR106 is presented in FIG. 5.

EXAMPLE 6

Construction of pHPR106A

The plasmid pHPR106A was constructed in substantial accordance with Example 2. However, the synthetic transcriptional activating sequence was constructed from the following single stranded DNA segments:

1. 5'-AATTCATACAGATAACCATCTGCGGTGATAAATTATCTCTGG CGGTGTTGACATAAATACCACTGGCGATTATAATGAGCACATCA-3'
2. 5'-GATCTGATGTGCTCATTATAATCGCCAGTGGTATTTATGTCAA CACCGCCAGAGATAATTTATCACCGCAGATGGTTATCTGTATG-3'.

The restriction site and function map of pHPR106A is identical to that presented in FIG. 5.

EXAMPLE 7

Construction of Plasmids psyn3 and psynC

A. Preparation of EcoRI-BglII Digested Plasmid pL110.

The 6.0 Kb EcoRI-BglII restriction fragment of plasmid pL110 can be prepared in substantial accordance with the methods of Example 2A, substituting pL110 DNA for pCZR125 DNA. The plasmid pL110 was claimed, and the methods and starting materials for its construction were disclosed by U.S. Pat. No. 4,874,703, which issued on Oct. 17, 1989. This patent is incorporated herein by reference.

B. Preparation of the Transcriptional Activating Sequence DNA

A synthetic transcriptional activating sequence was constructed from the following single stranded DNA segments:

(1) 5'-AATTCAAAAAATAAATTCCATATAAAAAACATACAGTTAACCA TCTGCGGTGATAAATATTTATCTCTGGCGGTGTTGACATA-3'
(2) 5'-TACCACTGGCGGTGATATAATG-3'
(3) 5'-AGCACATCA-3'
(4) 5'-ATTTATCACCGCAGATGGTTAACTGTATGTTTTTTATATGAA TTTATTTTTTG-3'
(5) 5'-CAACACCGCCAGAGATAAAT-3'
(6) 5'-TCACCGCCAGTGGTATATGT-3'
(7) 5'-GATCTGATGTGCTCATTATA-3'

These oligonucleotides were synthesized on an automated DNA synthesizer (Applied Biosystems, 850 Lincoln Center Dr., Foster City Calif. 94404) by the method described in Example 2B. Alternatively, the oligonucleotides can be synthesized by the modified phosphotriester method using fully protected trideoxynucleotide building blocks in substantial accordance with the methods of Itakura et al., 1977, *Science,* 198:1058 and Crea et al., 1978, *Pro. Natl. Acad. Sci. USA,* 75:5765. The synthetic DNA segments were dissolved in TE buffer and stored at 0° C.

One nmole each of synthetic oligonucleotides 2–6 were phosphorylated by treatment with 1 μl (~10 units) of T4 polynucleotide kinase in 50 mM Tris-HCl (pH 7.6), 10 mM MgCl$_2$, 10 mM dithiothreitol (DTT) and 0.3 mM adenosine 5'-triphosphate (ATP) in a total volume of 100 μl for 30 minutes at 37° C. This incubation was followed by a 10 minute incubation at 65° C. and subsequent freezing. One nmole of each of the phosphorylated oligonucleotides was mixed with 1.2 nmole of unphosphorylated oligonucleotides 1 and 7 in a reaction buffer containing 50 mM Tris-HCl (pH 7.6), 10 mM MgCl$_2$, 10 mM DTT, 0.5 mM ATP and 10 units of T4 DNA ligase. The reaction was incubated at 4° C. overnight. After the incubation, the ligated 113 base pair double stranded DNA fragment was purified by gel electrophoresis on a 15% polyacrylamide gel. The DNA fragment was cut out of the gel and was recovered by extraction with 2M triethyl ammonium bicarbonate buffer (pH 7.9) followed by desalting on a DE-52 column as described by Brown et al. (Brown, E. et al. *Methods in Enzymology* 68:101). After isolation, the DNA fragment was phosphorylated with T4 polynucleotide kinase as described above. Following the kinase reaction, the DNA was passed through a Sephadex G-50 column (Pharmacia, P-L Biochemicals, Inc., 800 Centennial Avenue, Piscataway, N.J. 08854) and the isolated DNA was stored in 50 μl of 10 mM Tris-HCl (pH 8.0).

This DNA fragment can also be constructed in substantial accordance with the methods of Example 2 from the following synthetic DNA segments:

1) 5'-AATTCAAAAAATAAATTCATATAAAAAA CATACAGTTAACCATC TGCGGTGATAAATATTTATCTCTGGCGGTGTTGACATATAC CACTGGCGGTGATA TAATGAGCACATCA-3';
2) 5'-GATCTGATGTGCTCATTATATCACCGCCAGTGGTATATGTCA ACACCGCCAGAGATAAATATTTATCACCGCAGATGGT TAACTGTATGTTTTTTAT ATGAATTTATTTTTTG-3'.

C. Final Construction of psyn3

Two μg of the restriction fragment prepared in Example 6A and 1 μg of the kinased DNA fragment prepared in Example 6B were ligated in substantial accordance with the method of Example 2C. A portion of the ligated DNA was used to transform *Escherichia coli* K12 RV308 cells according to the method of Example 1E. Tetracycline resistant transformants were selected and their plasmid DNA isolated according to the miniprep DNA isolation procedure of Example 1F. Restriction enzyme analysis was performed to confirm the structure of psyn3.

D. Construction of Plasmid psynC

Preferably, the synthetic DNA fragment prepared in Example 6B can be ligated with the DNA prepared in Example 2A in substantial accordance with the method described in Example 2C to form the plasmid psynC. A portion of the ligated DNA is used to transform *Escherichia coli* K12 RV308 cells according to the method of Example 1E. Tetracycline resistant transformants are selected and their plasmid DNA is isolated according to the miniprep DNA isolation procedure of Example 1F. Restriction enzyme analysis is performed to confirm the structure of psynC. A restriction site and function map of psynC is presented in FIG. 6.

EXAMPLE 8

Construction of Plasmids psyn4 and psynD

Plasmid psyn4 was constructed to eliminate the $O_L3$ operator region from the transcriptional activating sequence of plasmid psyn3. Ten μg of plasmid psyn3 (Example 6) was digested to completion with 10 μl (100 units) of HpaI in a 50 μl reaction volume containing 10 mM Tris-HCl (pH 7.4), 20 mM KCl, 10 mM MgCl$_2$, and 1 mMDTT. The mixture was incubated at 37° C. for 1 hour. The resulting DNA fragments (4168 base pairs and 1924 base pairs) were isolated by preparative gel electrophoresis in accordance with the methods described in Example 1A.

About 5 μg of the 4168 base pair HpaI-digested fragment DNA was further digested with 5 μl (50 units) of SspI in a 50 μl reaction volume containing 10 mM Tris-HCl (pH 7.4), 100 mMNaCl, 10 mMMgCl$_2$, and 10 mM β-mercaptoethanol. The mixture was incubated at 37° C. for 1 hour. The 4148 base pair HpaI-SspI restriction fragment was isolated by the preparative gel electrophoresis method described in Example 1A. This DNA fragment was ligated to the previously isolated 1924 base pair HpaI-digested DNA fragment of psyn3 with T4 DNA ligase in substantial accordance with the procedure described in Example 1C to form the plasmid psyn4. A portion of the ligated DNA was used to transform *Escherichia coli* RV308 cells according to the method of Example 1E. Tetracycline resistant transformants were selected and the plasmid DNA isolated according to the miniprep DNA isolation procedure of Example 1F. Restriction enzyme analysis was performed to confirm the structure of psyn4.

A more preferred vector that provides a transcriptional activating sequence identical to that of psyn4 is the plasmid psynD. The plasmid psynD is constructed in substantial accordance with Example 2. However, the transcriptional activating sequence is constructed from the following synthetic single stranded DNA segments:

1) 5'-AATTCAAAAAATAAATTCATATAAAAAA-CATACAGTTATT TATCTCTGGCGGTGTTGACAT-AAATACCACTGGCGGTTATAATGAGCA-CATCA-3'

2) 5'-GATCTGATGTGCTCATTATAACCGC-CAGTGGTATTTATGTCA ACACCGCCA-GAGATAAATAACTGTATGTTTTTTATAT-GAATTTATTTTTG-3'.

The plasmids psyn4 and psynD include a modified bacteriophage promoter-operator region wherein the $O_L3$ repressor binding region has been deleted. The activating sequence further comprises a −10 consensus sequence. A restriction and function map of psynD is presented in FIG. 7.

EXAMPLE 9

Analysis of Vector Stability

Analysis of expression vectors was carried out from restriction analysis of the vectors isolated from the fermentation mixture at the end of fermentation. The use of restriction analysis to characterize expression vectors is well known in the art. The methodology for the generation and the interpretation of restriction endonuclease mapping is well known in the art. Maniatis et al., 1982, provide a review of this subject.

The structural stability of the vectors of the present invention was analyzed by isolating the vector DNA from cells in the fermentation mixture at the end of fermentation. This DNA was isolated by the DNA miniprep procedure in substantial accordance with the method presented in Example 1F.

Restriction enzyme analysis was carried out by digesting isolated vector DNA with the restriction enzyme BamHI. Approximately 0.25 μg of the isolated vector DNA was digested to completion with 1 μl (10 units) of BamHI in a 10 μl reaction volume containing 6 mM Tris-HCl (pH 7.9), 150 mM NaCl, and 6 mM MgCl$_2$. The mixture was incubated at 37° C. for one hour. The digested DNA was fractionated on an agarose gel and visualized as described in Example 1A.

Based on the restriction map of the plasmids described herein, a BamHI restriction digest resulted in two DNA fragments for those plasmids that remain stable through the fermentation process. The BamHI digestion of plasmids pHPR104 and pHPR106A produced the expected DNA fragment of 4278 and 1808 base pairs. The BamHI digestion of plasmid psynC produces DNA fragments of 4278 and 1833 base pairs, while the digestion psynD produces DNA fragments of 4278 and 1814 base pairs. These results indicate that plasmids pHPR104, pHPR106A, psynC and, psynD remain stable through the fermentation process.

We claim:

1. A transcriptional activating sequence that is selected from the group consisting of:

```
5'-CATACAGATAACCATCTGCGGTGATAAATTA
   ||||||||||||||||||||||||||||||
3'-GTATGTCTATTGGTAGACGCCACTATTTAAT

TCTCTGGCGGTGTTGACA
        ||||||||||||||||||
        AGAGACCGCCACAACTGT

TAAATACCACTGGCGGTGATACTGAGCACATCA-3'
   ||||||||||||||||||||||||||||||||
   ATTTATGGTGACCGCCACTATGACTCGTGTAGT-5';

5'-CATACAGATAACCATCTGCGGTGATAAATTATC
   |||||||||||||||||||||||||||||||||
3'-GTATGTCTATTGGTAGACGCCACTATTTAATAG

TCTGGCGGTGTTGACA
        ||||||||||||||||
        AGACCGCCACAACTGT

TAAATACCACTGGCGGTGGTACTGAGCACATCA-3'
   ||||||||||||||||||||||||||||||||
   ATTTATGGTGACCGCCACCATGACTCGTGTAGT-5';

5'-CATACAGATAACCATCTGCGGTGATAAATTATC
   |||||||||||||||||||||||||||||||||
3'-GTATGTCTATTGGTAGACGCCACTATTTAATAG

TCTGGCGGTGTTGACA
        ||||||||||||||||
        AGACCGCCACAACTGT

TAAATACCACTGGCGGTTATAATGAGCACATCA-3'
   ||||||||||||||||||||||||||||||||
   ATTTATGGTGACCGCCAATATTACTCGTGTAGT-5';

5'-CATACAGATAACCATCTGCGGTGATAAATT
   ||||||||||||||||||||||||||||||
3'-GTATGTCTATTGGTAGACGCCACTATTTAA
```

-continued

```
          ATCTCTGGCGGTGTTGACA
          |||||||||||||||||||
          TAGAGACCGCCACAACTGT

TAAATACCACTGGCGATTATAATGAGCACATCA-3'
          ||||||||||||||||||||||||||||||||
          ATTTATGGTGACCGCTAATATTACTCGTGTAGT-5';
```

```
5'-CAAAAAATAAATTCATATAAAA
   ||||||||||||||||||||||
3'-GTTTTTTATTTAAGTATATTTT

AACATACAGTTATTTATCTCTGG
          |||||||||||||||||||||||
          TTGTATGTCAATAAATAGAGACC

CGGTGTTGACATAAATACCACTG
          |||||||||||||||||||||||
          GCCACAACTGTATTTATGGTGAC

GCGGTTATAATGAGCACATCA-3'
                    |||||||||||||||||||||
                    CGCCAATATTACTCGTGTAGT-5';
``` wherein A is deoxyadenyl; G is deoxyguanyl; C is deoxycytidyl; T is thymidyl.

2. The transcriptional activating sequence of claim 1 that is

```
5'-CATACAGATAACCATCTGCGGTGATAAATTATCTCTGGCGGTGTTGACA
   |||||||||||||||||||||||||||||||||||||||||||||||||
3'-GTATGTCTATTGGTAGACGCCACTATTTAATAGAGACCGCCACAACTGT

TAAATACCACTGGCGGTGATACTGAGCACATCA-3'
|||||||||||||||||||||||||||||||||
ATTTATGGTGACCGCCACTATGACTCGTGTAGT-5'.
```

3. The transcriptional activating sequence of claim 1 that is

```
5'-CATACAGATAACCATCTGCGGTGATAAATTATCTCTGGCGGTGTTGACA
   |||||||||||||||||||||||||||||||||||||||||||||||||
3'-GTATGTCTATTGGTAGACGCCACTATTTAATAGAGACCGCCACAACTGT

TAAATACCACTGGCGGTGGTACTGAGCACATCA-3'
|||||||||||||||||||||||||||||||||
ATTTATGGTGACCGCCACCATGACTCGTGTAGT-5'.
```

4. The transcriptional activating sequence of claim 1 that is

```
5'-CATACAGATAACCATCTGCGGTGATAAATTATCTCTGGCGGTGTTGACA
   |||||||||||||||||||||||||||||||||||||||||||||||||
3'-GTATGTCTATTGGTAGACGCCACTATTTAATAGAGACCGCCACAACTGT

TAAATACCACTGGCGGTTATAATGAGCACATCA-3'
|||||||||||||||||||||||||||||||||
ATTTATGGTGACCGCCAATATTACTCGTGTAGT-5'.
```

5. The transcriptional activating sequence of claim 1 that is

```
5'-CATACAGATAACCATCTGCGGTGATAAATTATCTCTGGCGGTGTTGACA
   |||||||||||||||||||||||||||||||||||||||||||||||||
3'-GTATGTCTATTGGTAGACGCCACTATTTAATAGAGACCGCCACAACTGT

TAAATACCACTGGCGATTATAATGAGCACATCA-3'
|||||||||||||||||||||||||||||||||
ATTTATGGTGACCGCTAATATTACTCGTGTAGT-5'.
```

6. The transcriptional activating sequence of claim 1 that is

```
5'-CAAAAAATAAATTCATATAAAAAACATACAGTTATTTATCTCTGG
    ||||||||||||||||||||||||||||||||||||||||||||
3'-GTTTTTTATTTAAGTATATTTTTTGTATGTCAATAAATAGAGACC

CGGTGTTGACATAAATACCACTGGCGGTTATAATGAGCACATCA-3'
   ||||||||||||||||||||||||||||||||||||||||||||
GCCACAACTGTATTTATGGTGACCGCCAATATTACTCGTGTAGT-5'.
```

7. A recombinant DNA expression vector that comprises a transcriptional activating sequence consisting of a DNA sequence selected from a transcriptional activating sequence of claim 1.

8. A recombinant DNA expression vector of claim 7 that sequentially comprises:

a) said transcriptional activating sequence, b) a translational activating sequence, and c) a DNA sequence that codes for a functional polypeptide, such that a) and b) are positioned for the expression of c).

9. A recombinant DNA expression vector of claim 8 that is a plasmid.

10. The plasmid of claim 9 that is pHPR104.
   11. The plasmid of claim 9 that is pHDM159.
   12. The plasmid of claim 9 that is pHPR106.
   13. The plasmid of claim 9 that is pHPR106A.
   14. The plasmid of claim 9 that is psynD.
   15. A host cell transformed with the vector of claim 8.
   16. The host cell of claim 15 that is *Escherichia coli*.
   17. The host cell of claim 16 that is *Escherichia coli* K12 RV308.
   18. The host cell of claim 17 that is *E. coli* K12 RV308/pHPR104.
   19. The host cell of claim 17 that is *E. coli* K12 RV308/pHDM159.
   20. The host cell of claim 17 that is *E. coli* K12 RV308/pHPR106.
   21. The host cell of claim 17 that is *E. coli* K12 RV308/pHPR106A.
   22. The host cell of claim 17 that is *E. coli* K12 RV308/psynD.

23. A method of producing a functional polypeptide comprising: culturing the host cell of claim 16 under conditions that enable the expression of the encoded polypeptide.

24. A method of claim 23 wherein the DNA sequence that codes for a functional polypeptide encodes: β-galactosidase, human preproinsulin, human proinsulin, human insulin A-chain, human insulin B-chain, non-human insulin, human growth hormone, insulin-like growth factors, human interferon, viral antigens, urokinase, tissue-type plasminogen activator, interleukins 1–6, colony stimulating factors, erythropoetin, human transferrin, and EK-BGH.

25. A method of claim 24 wherein the DNA sequence that codes for a functional polypeptide encodes EK-BGH.

26. The recombinant DNA expression vector pHPR97.

* * * * *